United States Patent [19]
Jacobson et al.

[11] Patent Number: 5,120,745
[45] Date of Patent: Jun. 9, 1992

[54] 1-DIMETHYLCARBAMOYL-3-SUBSTITUT-ED-5-SUBSTITUTED-1H-1,2,4-TRIAZOLES

[75] Inventors: Richard M. Jacobson, Chalfont; Luong T. Nguyen, Lansdale; Muthuvelu Thirugnanam, Langhorne, all of Pa.

[73] Assignee: Shell Internationale Research Maatschappij B.V., Netherlands

[21] Appl. No.: 589,149

[22] Filed: Sep. 27, 1990

Related U.S. Application Data

[63] Continuation of Ser. No. 181,872, Apr. 15, 1988, Pat. No. 4,970,224.

[51] Int. Cl.$^5$ .............. A01N 43/653; A01N 43/42; A01N 43/40; C07D 403/12; C07D 401/12
[52] U.S. Cl. .................. 514/314; 514/297; 514/307; 514/309; 514/310; 514/311; 514/312; 514/313; 514/326; 514/340; 514/384; 546/102; 546/104; 546/105; 546/106; 546/107; 546/141; 546/142; 546/143; 546/145; 546/146; 546/147; 546/148; 546/153; 546/155; 546/156; 546/157; 546/159; 546/168; 546/169; 546/170; 546/141; 546/174; 546/175; 546/210; 546/276; 548/264.2; 548/264.4

[58] Field of Search ............... 546/276, 102, 104, 105, 546/106, 107, 141, 142, 143, 145, 146, 147, 148, 153, 155, 156, 157, 159, 168, 169, 170, 171, 174, 175, 210; 548/264.2, 264.4; 514/340, 384, 297, 307, 309, 310, 311, 312, 313, 314, 326

[56] References Cited

U.S. PATENT DOCUMENTS 4,742,072  5/1988  Jacobson et al. .............. 514/384

*Primary Examiner*—Patricia L. Morris

[57] ABSTRACT

This invention relates to 1-dimethylcarbamoyl-3-substituted-5-substituted-1H-1,2,4-triazoles of the formula

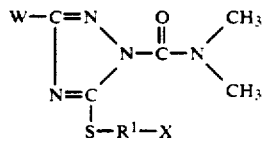

wherein the substituents are as defined herein, compositions containing those compounds and methods of use.

20 Claims, No Drawings

1-DIMETHYLCARBAMOYL-3-SUBSTITUTED-5-SUBSTITUTED-1H-1,2,4-TRIAZOLES

This is a continuation of application Ser. No. 181,872, filed Apr. 15, 1988, now U.S. Pat. No. 4,970,224.

BACKGROUND OF THE INVENTION

This invention relates to novel 1-dimethyl-carbamoyl-3-substituted-5-substituted-1H-1,2,4triazoles which are useful as insecticides, compositions containing those compounds and methods of use.

Certain 1,2,4-triazoles have been disclosed as having pesticidal activity.

U.S. Pat. No. 3,308,131 describes a group of 1,2,4-triazoles having the general formula $$\begin{array}{c}N\text{———}C\text{—}R^3 \\ \parallel \quad\quad \parallel \\ R^4\text{—}C \quad\quad N \\ \diagdown \quad \diagup \\ N \\ \mid \\ C\text{=}X \\ \mid \\ N \\ \diagup \diagdown \\ R^1 \quad R^2\end{array} \quad \text{and} \quad \begin{array}{c}N\text{====}C\text{—}R^3 \quad R^1 \\ \mid \quad\quad\quad \diagup \\ R^4\text{—}C \quad N\text{—}C\text{—}N \\ \diagdown \diagup \quad\quad \parallel \quad \diagdown \\ N \quad X \quad R^2\end{array}$$

where X is oxygen or sulfur, $R^1$ and $R^2$ are aliphatic groups containing up to 14 carbons and which may be joined to form a heterocyclic ring with the carbamoyl nitrogen atom and $R^3$ and $R^4$, which together contain up to 14 carbon atoms, are free from aliphatic unsaturation and are selected from hydrogen, halogen, sulfonyl, mercapto, cyano, hydrocarbyl, halohydrocarbyl, nitrohydrocarbyl, hydroxycarbyloxycarbonylhydrocarbyl, hydrocarbylsulfonyl, hydrocarbylmercapto, nitrohydrocarbylmercapto, halohydrocarbylmercapto, aminohydrocarbylmercapto and hydrocarbyloxyhydrocarbyl. These compounds are disclosed to be useful as insecticides, in dyeing textiles and as analgesics.

U.S. Pat. No. 4,291,043 discloses 1-N,N-dimethylcarbamoyl-3(5)-alkyl-5(3)-alkylthioalkylthio-1,2,4-triazoles having insecticidal activity. The 3(5) substituents include i-propyl, s-butyl, t-butyl or optionally methyl-substituted cyclopropyl and a group having the formula $$-S-CH(R')-(CH_2)_n-S-R''$$

where R' is H or methyl, R" is lower ($C_1$-$C_4$)alkyl and n is zero or one.

U.S. Pat. Nos. 3,973,028 and 4,038,387 disclose 1-dimethylcarbamoyl-3-branched alkyl-1,2,4-triazole-5-yl-(N-substituted)sulfonamides having insecticidal activity. The branched alkyl groups include $C_3$ to $C_4$ secondary or tertiary alkyl and cycloalkyl.

U.S. Pat. No. 4,054,664 discloses 1(2)-(N,N-disubstituted carbamoyl)-3,5-substituted-1,2,4-triazoles having insecticidal activity. The 3(5) substituents include isopropyl, s-butyl, t-butyl and S-R where R is methyl, ethyl, propyl, vinyl, prop-2-ynyl, but-2-enyl or 2-haloalkyl.

U.S. Pat. No. 4,255,435 discloses 1(2)-N,N-disubstituted carbamoyl)-3,5-substituted-1,2,4triazoles having activity against a variety of economically important insects and nematodes. The 3(5) substituents include i-propyl, s-butyl, t-butyl. The 5(3) substituents include SR where R is methyl, ethyl, propyl, vinyl, 2-propynyl, 2-butenyl and 2-haloallyl.

U.S. Pat. No. 4,160,839 discloses 1-N,N-dimethylcarbamyl-3,5-substituted-1,2,4-triazoles having insecticidal activity. The 3-substituents include t-butyl, propyl, cyclopropyl, isopropyl or 1-methylpropyl. The 5-substituents include S-R where R is 2-propynyl, allyl, 2-bromoallyl, 2-chloroallyl, 2-methylallyl, 1-methylallyl or 2,3,3-trichloroallyl.

U.S. Pat. Nos. 4,220,790 and 4,066,774 disclose 1-N,N-dimethylcarbamoyl-3-tert-butyl-5-methylthio-1,2,4-triazole having insecticidal activity and a method of killing insects using said triazole.

DE 3031191A1 discloses 1-dimethylcarbamoyl-3(or 5)-benzylthio-5(or 3)-alkyl-1,2,4-triazoles having insecticidal activity. The 5(or 3) substituents include isopropyl, s-butyl, t-butyl, or optionally methyl substituted cyclopropyl.

DE 3021232 discloses 1-dimethylcarbamoyl-1,2,4triazoles having insecticidal activity. The 3(or 5) position is substituted with the group $$\begin{array}{c}-SCH-(CH_2)_n-SR_1 \\ \mid \\ R_2\end{array}$$

wherein $R^1$ is ($C_1$-$C_4$)alkyl, $R^2$ is hydrogen or methyl and n is 0 or 1.

EP 0029407 discloses 1-N,N'-dimethylcarbamoyl-3,5-substituted-1,2,4-triazoles having insecticidal activity. The 3-substituents include i-propyl, s-butyl, t-butyl or cyclopropyl. The 5-substituents include $S(CH_2)_nOR_2$ where $R_2$ is ($C_1$-$C_3$)alkyl and n is 1 or 2.

The present invention relates to 1-dimethyl-carbamoyl-3-substituted-5-substituted-1H-1,2,4triazoles. These compounds are distinguished primarily by their novel 5-position substituents.

Compounds of the present invention are also distinguished by their insecticidal activity against sucking insects such as those of the order Homoptera and especially those of the family Aphididae. Accordingly, compounds of the present invention are particularly suitable for controlling plant-destructive insects in crops of cultivated plants and ornamentals, especially in crops of fruit and vegetables.

It is therefore an objective of the present invention to provide novel compounds, and compositions containing said compounds, which possess insecticidal activity. It is a further objective of this invention to provide methods for controlling insects using the novel compounds.

SUMMARY OF THE INVENTION

In accordance with the present invention, there are provided compounds having the formula $$\begin{array}{c}W-C=N \quad\quad O \quad CH_3 \\ \mid \quad\quad\quad \diagdown \quad \parallel \quad \diagup \\ \quad\quad\quad\quad N-C-N \\ \mid \quad\quad\quad \diagup \quad\quad \diagdown \\ N=C \quad\quad\quad\quad CH_3 \\ \mid \\ S-R^1-X\end{array} \quad \text{I}$$

wherein

W is t-butyl, s-butyl, i-propyl, cyclopropyl, 1-methylthio-1-methylethyl or 1-methylcycloprop-1-yl;

$R^1$ is unsubstituted or substituted —$(CH_2)_n$— having from one to four of the same or different substituents independently selected from cyano, nitro, halo, —OR, —$CO_2R$, —OCOR, —COR, ($C_2$-$C_6$)alkenyl, ($C_2$-$C_6$)alkynyl, ($C_1$-$C_6$)alkyl, ($C_1$-$C_6$)haloalkyl and unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —$CO_2R$, —COR, —OCOR, ($C_1$-$C_4$)alkyl, ($C_1$-$C_4$)-alkoxy, ($C_1$-$C_4$)haloalkyl or ($C_2$-$C_6$)alkenyl and X is unsubstituted ($C_1$-$C_4$)dialkoxyalkyl having independently the stated number of carbon atoms in each alkyl group; substituted ($C_1$-$C_4$)-dialkoxyalkyl having independently the stated number of carbon atoms in each alkyl group and having one to three substituents; unsubstituted 5- to 14-membered heterocycle; or substituted 5- to 14-membered heterocycle having one to three substituents; the heterocycle having one to three of the same or different heteroatoms independently selected from oxygen, nitrogen and sulfur; where the substituent on the dialkoxyalkyl or the heterocycle is independently selected from halo, cyano, nitro, amino, —$NRCOR^2$, —COOR, —$CONRR^2$, —COR, ($C_1$-$C_4$)alkyl, ($C_1$-$C_4$)alkoxy, ($C_1$-$C_4$)alkylthio, ($C_1$-$C_4$)haloalkyl, ($C_1$-$C_4$)haloalkoxy, ($C_1$-$C_4$)-polyhaloalkyl and ($C_1$-$C_4$)polyhaloalkoxy;

where

R and $R^2$ are the same or different and are hydrogen; unsubstituted or substituted ($C_1$-$C_6$)alkyl having one to three substituents; or unsubstituted or substituted phenyl having one to three substituents; where the substituent is independently selected from halo, cyano, nitro, hydroxy, trifluoromethoxy, difluoromethoxy, tetrafluoroethoxy, trifluoromethylthio, tetrafluoroethylthio, ($C_1$-$C_4$)alkyl, ($C_1$-$C_4$)alkoxy, ($C_1$-$C_4$)haloalkyl, ($C_2$-$C_6$)alkenyl, carboxy, ($C_1$-$C_4$)alkoxycarbonyl;

n is an integer from one to six; and agronomically acceptable salts thereof.

Further, in accordance with the present invention, there are provided compositions containing compounds of the present invention and methods of using said compounds and compositions.

DETAILED DESCRIPTION OF THE INVENTION

The term "halo" includes fluoro, chloro, bromo and iodo. The term "alkyl" should be understood as including straight or branched chain groups such as methyl, ethyl, n-propyl, isopropyl, n-butyl, t-butyl, isobutyl, neopentyl, isooctyl and the like. The term "heterocycle" should be understood as including aromatic rings such as acridinyl, azepinyl, benzimidazolyl, benzisoxazolyl, benzodiazinyl, benzofuryl, benzopyranyl, benzopyronyl, benzothiazolyl, benzothiofuryl, benzoxazolyl, benzopyrazolyl, carbazolyl, dioxinyl, furyl, imidazolyl, indolyl, isobenzazolyl, isobenzofuryl, isobenzopyranyl, isobenzothiofuryl, isoindolyl, isoquinolyl, isoxazolyl, naphthriyidinyl, oxadiazolyl, oxazinyl, oxazolyl, oxepinyl, phthalimidolyl, pyranyl, pyrazinyl, pyrazolyl, pyridazinyl, pyridyl, pyrimidoyl, pyridinyl, pyronyl, pyrroyl, quinazolinyl, quinolyl, thiazolyl, thienyl, thiepinyl, thioxanthyl, triazinyl, triazolyl, xanthenyl and the like. The term "heterocycle" should also be understood to include partially and completely saturated derivatives of the heterocycles named above including but not limited to pyrrolidinyl, piperidinyl, morpholinyl, dioxolanyl, dioxanyl, tetrahydropyranyl, thiazolinyl, oxazolidinonyl, isoxazolinyl and the like.

Preferred are compounds of the invention where
W is t-butyl;

$R^1$ is unsubstituted or substituted —$(CH_2)_n$—having from one to four of the same or different substituents independently selected from ($C_1$-$C_6$)alkyl, ($C_1$-$C_6$)haloalkyl, halo, nitro and cyano;

X is unsubstituted or substituted ($C_1$-$C_8$)-dialkoxyalkyl having one to three substituents; unsubstituted or substituted heterocycle selected from triazolyl, pyridyl, dioxanyl, dioxolanyl, tetrahydropyranyl, oxazolidinonyl, isoxazolyl, furyl, pyrazinyl, phthalimidolyl and quinolyl; the heterocycle having from one to three substituents; where the substituent is independently selected from ($C_1$-$C_4$)alkyl and ($C_1$-$C_4$)haloalkyl; and n is an integer from one to six.

More preferred compounds include those of Formula I where

W is t-butyl;

$R^1$ is —$CH_2$—or —$CH(CH_3)$—, and

X is unsubstituted or ($C_1$-$C_4$)alkyl-substituted ($C_1$-$C_8$)dialkoxyalkyl, triazolyl, pyridyl, dioxolanyl, dioxanyl, tetrahydropyranyl, oxazolindinonyl, isoxazolyl, furyl, pyrazinyl, phthalimidolyl or quinolyl.

Most preferred compounds include those where

W is t-butyl;

$R^1$ is —$CH_2$—and

X is dioxanyl, dioxolanyl, furyl or triazolyl.

Since the 1-dimethylcarbamoyl-3-substituted-5-substituted-1H-1,2,4-triazoles of Formula I may possess acidic or basic functional groups, they may form novel salts with appropriate bases or acids which also exhibit insecticidal activity.

Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. Among the ammonium salts are those in which the ammonium cation has the formula $NR^9R^{10}R^{11}R^{12}$ wherein each of $R^9, R^{10}, R^{11}$ and $R^{12}$ are independently a hydrogen atom, a hydroxy group, a ($C_1$-$C_4$)alkoxy group, a ($C_1$-$C_{20}$)alkyl group, a ($C_3$-$C_8$)alkenyl group, a ($C_3$-$C_8$)alkynyl group, a ($C_2$-$C_8$)hydroxyalkyl group, a ($C_2$-$C_8$)alkoxyalkyl group, a ($C_2$-$C_6$)aminoalkyl group, a ($C_2$-$C_6$)haloalkyl group, an amino group, a ($C_1$-$C_4$)alkyl or ($C_1$-$C_4$)dialkylamino group, a substituted or unsubstituted phenyl group, a substituted or unsubstituted phenylalkyl group, having up to four carbon atoms in the alkyl moiety, or any two of $R^9, R^{10}, R^{11}$ or $R^{12}$ can be taken together to form with the nitrogen atom a 5- or 6-membered heterocyclic ring, optionally having up to one additional hetero atom (e.g., oxygen, nitrogen or sulfur) in the ring, and preferably saturated, such as piperidino, morpholino, pyrrolidino, piperazino or the like, or any three of $R^9, R^{10}, R^{11}$ or $R^{12}$ can be taken together to form with the nitrogen atom a 5- or 6-membered aromatic heterocyclic ring, such as piperazole or pyridine. When the ammonium group contains a substituted phenyl or substituted phenylalkyl group, the substituents will generally be selected from halogen atoms, ($C_1$-$C_8$)alkyl groups, ($C_1$-$C_4$)alkoxy groups, hydroxy groups, nitro groups, trifluoromethyl groups, cyano groups, amino groups, ($C_1$-$C_4$)alkylthio groups and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-ammonium butyl)-ammonium, methoxyethyl ammonium, diisopropylammonium, pyridinium, dialkyl ammonium, pyrazolium, propargylammonium, dimethyl hydrazinium, octadecylammonium, 4-dichlorophenylamxonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium and the like.

Among the acid addition salts are those in which the anion is an agronomically acceptable anion such as chloride, bromide, sulfate, nitrate, perchlorate, acetate, oxalate or the like.

In a preferred embodiment, the agronomically acceptable salts include the sodium, potassium, ammonium, alkylammonium, chloride and sulfate salts.

The 1-dimethylcarbamoyl-3-substituted-5-substituted-1H-1,2,4-triazoles of the present invention their precursors are prepared by alkylating the sulfur (S-alkylating) a 3-substituted-5-thio-1H-1,2,4-triazole in the presence of a solvent or diluent which is inert to the reactants and optionally an acid scavenger with a compound having the formula $$Z-R^1-X \qquad \text{II}$$

where $R^1$ and X are as defined above for formula I and Z is a good leaving group, to obtain 3-substituted-5-substituted-1H-1,2,4-triazoles. Leaving groups are described in "Basic Principles of Organic Chemistry" by Roberts and Caserio, W. A. Benjamin Inc., New York, 1965, p. 290, incorporated herein by reference. Examples of leaving groups include halo (chloro, bromo or iodo), alkyl sulfonate, aryl sulfonate or alkyl sulfate.

Suitable solvents or diluents for the above process include but are not limited to methanol, ethanol, ethyl acetate, tetrahydrofuran, dimethylformamide and acetonitrile and the like.

Suitable acid scavengers for the above process, such as triethylamine or diisopropylethylamine may be added during alkylation or, if desired, the 3-substituted-5-thio-1H-1,2,4-triazole can be pretreated with an acid scavenger such as sodium hydride, sodium hydroxide and the like.

Generally, equivalent molar amounts of starting materials in an overall concentration of from about 0.01 molar to about 5 molar are used, and the above process is carried out at from about 0° C. to about 150° C. for from about 5 minutes to about 2 days. Preferably the starting materials are present in a concentration of from about 0.1 molar to 1 molar and the reaction is carried out from about 20° C. to about 90° C.

Modifications to the above process may be necessary to accommodate reactive functionalities of particular 5-substituents. Such modifications would be apparent and known to those skilled in the art.

The 3-substituted-5-substituted-1H-1,2,4-triazole obtained by the above process is then reacted with a compound having the formula

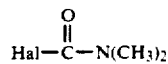

$$\text{Hal}-\overset{\overset{\displaystyle O}{\|}}{C}-N(CH_3)_2 \qquad \text{III}$$

where Hal is halogen (chloro, bromo or iodo), in the presence of a suitable acid scavenger and optionally a suitable acylation catalyst.

Suitable acid scavengers for this process include tertiary amines such as triethylamine and pyridine and the like.

Suitable acylation catalysts include tertiary amines such as 4-dimethylaminopyridine, 4-pyrrolidinopyridine, triethyl-amine, pyridine and the like. Generally, when the acylation catalyst is used, it is present in the reaction mixture in an amount from about 0.001 to about 0.25 molar equivalent of the starting material.

Generally, equivalent molar amounts of starting materials in an overall concentration of from about 0.01 molar to about 5 molar are used, and the above process is carried out at from about 0° C. to about 150° C. for from about 5 minutes to about 2 days. Preferably the starting materials are present in a concentration of from about 0.1 molar to 1 molar and the reaction is carried out from about 20° C. to about 90° C.

The compounds of Formula II can be prepared from known precursors by known methods.

The 3-substituted-5-thio-1H-1,2,4-triazoles used as a starting material can be prepared from known precursors by known methods as illustrated below in Example No. 1.

After preparing compounds embraced by Formula I by the above process, the salts of the invention can be prepared by any convenient art-recognized method, such as by reacting a metal hydroxide, a metal hydride or an amine or ammonium salt, such as a halide, hydroxide or alkoxide with the free acid, or reacting a quaternary ammonium salt, such as chloride, a bromide, nitrate or the like with a metal salt of the invention in a suitable solvent. When metal hydroxides are used as reagents, useful solvents include water, glyme, dioxane, tetrahydrofuran, methanol, ethanol, isopropanol and the like. When metal hydrides are used as reagents, useful solvents include nonhydroxylic solvents such as dioxane, glyme, tetrahydrofuran, diethyl ether, hydrocarbons such as toluene, xylene, hexane, pentane, heptane, octane, dimethylformamide and the like. When amines are used as reagents, useful solvents include alcohols, such as methanol or ethanol, hydrocarbons, such as toluene, xylene, hexane and the like, tetrahydrofuran, glyme, dioxane or water. When ammonium salts are used as reagents, useful solvents include water, alcohols, such as methanol or ethanol, glyme, tetrahydrofuran or the like. When the ammonium salt is other than a hydroxide or alkoxide, an additional base, such as potassium or sodium hydroxide, hydride or alkoxide is generally used. The particular choice of solvent will depend on the relative solubilities of the starting materials and the resultant salts and slurries rather than solutions of certain reagents which may be used to obtain the salts. Generally, equivalent amounts of the starting reagents are used and the salt-forming reaction is carried out at about 0° C. to about 100° C., preferably at about room temperature at atmospheric pressure.

The acid addition salts of the present invention can be prepared by any convenient art-recognized method such as by reacting hydrochloric, hydrobromic, sulfuric, nitric, phosphoric, acetic, propionic, benzoic or other suitable acid with a compound of the present invention having a basic functionality in a suitable solvent. Useful solvents include water, alcohols, ethers, esters, ketones, haloalkanes and the like. The particular choice of solvent will depend on the relative solubilities of the starting materials and the resulting salts and slurries rather than solutions of certain reagents which may be used to obtain the salts. Generally, equivalent molar amounts of starting materials are used and the salt-forming reaction is carried out at from about −100° C. to about 100° C., preferably at about room temperature.

The following examples will further illustrate this invention but are not intended to limit it in any way. In Table I, representative 1- dimethylcarbamoyl-3-substituted-5-substituted-1H-1,2,4-triazoles of the present invention are listed.

The structures of these compounds were confirmed by NMR and in some cases by IR and/or elemental analysis. Specific illustrative preparations of several of the compounds are described after Table I.

TABLE I

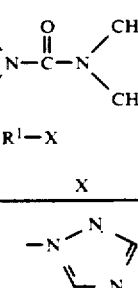

| No. | W | $R^1$ | X | m.p. °C. |
|---|---|---|---|---|
| 1. | t-butyl | —CH$_2$— | 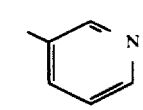 | 100–102 |
| 2. | t-butyl | —CH$_2$— | 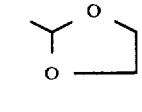 | 47–48 |
| 3. | t-butyl | —CH$_2$— | 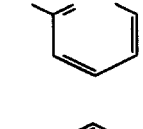 | Oil |
| 4. | t-butyl | —CH$_2$— | 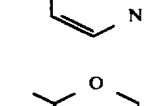 | Oil |
| 5. | t-butyl | —CH$_2$— | 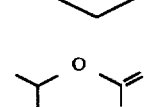 | Oil |
| 6. | t-butyl | —CH$_2$— | 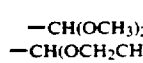 | Oil |
| 7. | t-butyl | —CH$_2$— | 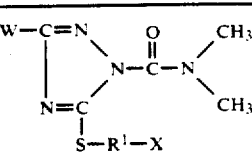 | 146–147 |
| 8. | t-butyl | —CH$_2$— | —CH(OCH$_3$)$_2$ | Oil |
| 9. | t-butyl | —CH$_2$— | —CH(OCH$_2$CH$_3$)$_2$ | Oil |

TABLE I-continued

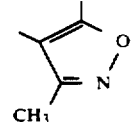

| No. | W | $R^1$ | X | m.p. °C. |
|---|---|---|---|---|
| 10. | t-butyl | —CH$_2$— | 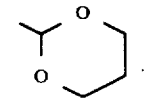 | 75–76 |
| 11. | t-butyl | —CH$_2$— | —C(CH$_3$)(OCH$_3$)$_2$ | Oil |
| 12. | t-butyl | —CH$_2$— | 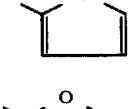 | 88–90 |
| 13. | t-butyl | —CH$_2$— | 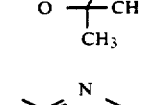 | Oil |
| 14. | t-butyl | —CH$_2$— | 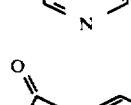 | Oil |
| 15. | t-butyl | —CH$_2$— | 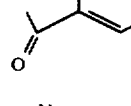 | Oil |
| 16. | t-butyl | —CH$_2$— | 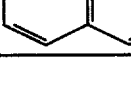 | Oil |
| 17. | t-butyl | —CH$_2$— |  | 117–121 |

EXAMPLE A

Preparation of 3-t-butyl-5-thio-1H-1,2,4triazole

To a suspension of thiosemicarbazide (500 grams (g), 5.49 mole) in 2 liters of tetrahydrofuran (THF) in a 5 liter round bottomed flask cooled by an ice bath to 10° C. internal was added trimethylacetyl chloride (694 g, 5.76 mole) over thirty minutes. The exotherm was controlled to below 40° C. Then 482 g (6.04 mole) of 50 percent aqueous NaOH was added over thirty minutes with the exotherm controlled to below 50° C. The cooling bath was then removed and the mixture was stirred for two hours. Heat was then applied and 600 ml of THF was removed by distillation before starting the addition of a solution of 1500 ml of water and 835 g of 50 percent NaOH over ninety minutes. Removal of the THF was continued during this period until the internal temperature reached 80° C. The mixture was then refluxed an additional three hours and then cooled to room temperature before transferring it into a 12 liter separatory funnel. Three kg of ice and 1500 ml of THF were added before the mixture was slowly acidified by 1500 ml of concentrated hydrochloric acid. The aqueous phase was separated and extracted with 2 liters of ethyl acetate before being discarded. The combined organic layers were then washed with 2 liters of brine and dried over magnesium sulfate (500 g) and then concentrated in vacuo to afford 698 g of white solid 3-t-butyl-5-thio-1H-1,2,4-triazole, m.p. 20° C.

EXAMPLE NO. 1

Preparation of 1-dimethylcarbamoyl-3t-butyl-5-(1,3-dioxolan-2-yl-methylthio)-1H-1,2,4triazole (Compound 3)

1.4 g (35 mmole) of 60 percent sodium hydride in mineral oil was washed twice with hexanes and then suspended in 10 ml of dimethylformamide (DMF). A solution of 5 g (31.8 mmole) of 3-t-butyl-5-thio-1H-1,2,4-triazole in 10 ml of DMF was added slowly and allowed to stir at room temperature until hydrogen evolution ceased, then 5.3 g (31.7 mmole) of 2-bromomethyl-1,3-dioxolane was added and the reaction was refluxed for three hours. The solvent was removed in vacuo and the resulting mixture was partitioned between methylene chloride and water. The organic layer was separated, dried over magnesium sulfate and concentrated. Trituration with ether/hexane afforded 7.5 g of solid 3-t-butyl-5-(1,3-dioxolan-2-yl-methylthio)-1H-1,2,4-triazole.

3-t-Butyl-5-(1,3-dioxolan-2-yl-methylthio)-1H-1,2,4-triazole (7 g, 28.8 mmole), 2.8 ml (30.5 mmole) of dimethylcarbamoyl chloride, 8 ml (57 mmole) of triethylamine and 0.5 g (4.1 mmole) of 4-dimethylaminopyridine were dissolved in 50 ml of tetrahydrofuran (THF). The mixture was refluxed for four hours, concentrated in vacuo and partitioned between methylene chloride and dilute hydrochloric acid. The organic layer was separated, dried over magnesium sulfate, filtered and concentrated. Chromatography on silica gel using ethyl ether/hexane gave 1-dimethylcarbamoyltriazole, an oil.

EXAMPLE NO. 2

Preparation of 1-dimethylcarbamoyl-3-t-butyl-5-(pyrid-2-yl-methylthio)-1H-1,2,4-triazole (Compound 4)

A suspension of 5 g (31.8 mmole) of 3-t-butyl-5-thio-1H-1,2,4-triazole and 5 g (30.5 mmole) of 2-picolyl chloride hydrochloride in 50 ml of THF was refluxed for three hours. The mixture was cooled to 10° C. and diluted with 50 ml of hexane. The resulting solid was filtered off to yield 10 g of 3-t-butyl-5-(pyrid-2-yl-methylthio)-1H-1,2,4-triazole dihydrochloride, m.p. 190°-192° C.

Ten g of 3-t-butyl-5-(pyrid-2-yl-methylthio)-1H-1,2,4-triazole dihydrochloride, 0.5 g (4.1 mmole) of 4-dimethylaminopyridine, 10 g (100 mmole) of triethylamine, 3.5 g of dimethylcarbamoyl chloride and 100 ml of THF were refluxed for two hours. The mixture was concentrated in vacuo, and partitioned between ether and water. The organic layer was washed with brine, dried over magnesium sulfate, filtered and the solvent was removed in vacuo to yield 1-dimethyl-carbamoyl-3-t-butyl-5-(pyrid-2-yl-methylthio)-1H-1,2,4triazole, an oil.

EXAMPLE NO. 3

Preparation of 1-dimethylcarbamoyl-3-t-butyl-5-(fur-2-yl-methylthio)-1H-1,2,4-triazole (Compound 13)

Five g (31.8 mmole) of 3-t-butyl-5-thio-1H-1,2,4-triazole was dissolved in 50 ml of ethyl acetate and 6 ml (34 mmole) of diisopropylethylamine. To this was added 3.7 g of technical 2-chloromethylfuran (ca 35 mmole) and the mixture was allowed to stir for eighteen hours. The mixture was washed with water and brine, dried over magnesium sulfate, concentrated in vacuo and triturated with ether/hexane to yield 3-t-butyl-5-(fur-2-yl-methylthio)-1H-1,2,4-triazole, a solid.

3-t-Butyl-5-(fur-2-yl-methylthio)-1H-1,2,4-triazole was reacted with dimethylcarbamoyl chloride by substantially the same procedure as described in Example 1 to yield 1-dimethylcarbamoyl-3-t-butyl-5-(fur-2-yl-methylthio)-1H-1,2,4-triazole, an oil.

EXAMPLES 4-11

Compounds 6-12 and 14, as listed below, were made using essentially the method of Example 1 using the appropriate halomethylheterocycle.

| Cmpd No. | Name | Starting Mat'l Hal | Reaction Temp | Time |
|---|---|---|---|---|
| 6 | 1-dimethylcarbamoyl-3-t-butyl-5-(tetrahydro-pyran-2-yl-methylthio)-1H-1,2,4-triazole | Br | Reflux | 5 hrs. |
| 7 | 1-dimethylcarbamoyl-3-t-butyl-5-(oxazolidinon-5-yl-methylthio)-1H-1,2,4-triazole | Cl | 100° C. | 5 hrs. |
| 8 | 1-dimethylcarbamoyl-3-t-butyl-5-(2,2-dimethoxy-ethylthio)-1H-1,2,4-triazole | Br | 60° C. | 3 hrs. |
| 9 | 1-dimethylcarbamoyl-3-t-butyl-5-(2,2-diethoxy-ethylthio)-1H-1,2,4-triazole | Br | 80° C. | 5 hrs. |
| 10 | 1-dimethylcarbamoyl-3-t-butyl-5-(3,5-dimethyl-isoxazol-4-yl-methylthio)-1H-1,2,4-triazole | Cl | 70° C. | 4 hrs. |
| 11 | 1-dimethylcarbamoyl-3-t-butyl-5-(2,2-dimethoxy-propylthio)-1H-1,2,4-triazole | Br | 80° C. | 4 hrs. |
| 12 | 1-dimethylcarbamoyl-3-t-butyl-5-(1,3-dioxan-2-yl-methylthio)-1H-1,2,4-triazole | Br | Reflux | 4 hrs. |
| 14 | 1-dimethylcarbamoyl-3-t-butyl-5-(4,4-dimethyl-1,3-dioxolan-2-yl-methylthio)-1H-1,2,4-triazole | Cl | 80° C. | 4 hrs. |

EXAMPLES 12-15

Compounds 1, 2, 5 and 17, as listed below, were made using essentially the method of Example 2 using the appropriate halomethyl heterocycle.

| Cmpd No. | Name | Starting Mat'l Hal | Time |
|---|---|---|---|
| 1 | 1-dimethylcarbamoyl-3-t-butyl-5-(1,2,4-triazole-1-yl-methylthio)-1H-1,2,4- | Cl(HClsalt) | 6 hrs. |

-continued

| Cmpd No. | Name | Starting Mat'l Hal | Time |
|---|---|---|---|
| 2 | 1-dimethylcarbamoyl-3-t-butyl-5-(pyrid-3-yl-methylthio)-1H-1,2,4-triazole | Cl(HClsalt) | 2 hrs. |
| 5 | 1-dimethylcarbamoyl-3-t-butyl-5-(pyrid-4-yl-methylthio)-1H-1,2,4-triazole | Cl(HClsalt) | 18 hrs. |
| 17 | 1-dimethylcarbamoyl-3-t-butyl-5-(quinol-2-yl-methylthio)-1H-1,2,4-triazole | Cl(HClsalt) | 18 hrs. |

EXAMPLES 16 and 17

Compounds 15 and 16, as listed below, were made using essentially the method of Example 3 using the appropriate halomethyl heterocycle and triethylamine in place of diisopropyl ethylamine.

| Cmpd No. | Name | Starting Mat'l Hal | Reaction Temp | Time |
|---|---|---|---|---|
| 15 | 1-dimethylcarbamoyl-3-t-butyl-5-(pyrazin-2-yl-methylthio)-1H-1,2,4-triazole | Cl | Reflux | 4 hrs. |
| 16 | 1-dimethylcarbamoyl-3-t-butyl-5-(phthalimido-methylthio)-1H-1,2,4-triazole | Cl | Reflux | 18 hrs. |

Surprisingly, many of the compounds of the present invention exhibit better insecticidal activity than the closest known compounds. Furthermore, the activity of these compounds, especially towards aphids, allows for plant protection without disturbing beneficial insects, making these compounds especially useful in integrated pest management programs. Beneficial insects include pollinators, for example, honeybees (*Apis mellifera*); predators, for example, the lady beetles (*Hippodamia convergons*); and parasites, for example, uga wasp (*Uga menoni*).

In particular, the compounds of the invention are active against sucking insects of the order Homoptera, especially hoppers (Suborder: *Auchenorrhyncha*) and aphid (Suborder: *Sternorrhyncha*). The 1-dimethylcarbamoyl-3-substituted-5-substituted-1H-1,2,4-triazoles of the present invention show, for example, activity at a concentration of from about 1 part per million (ppm) to about 21.0 ppm against Green Peach Aphids. Activity against potato and apple leafhoppers has also been observed. Accordingly, compounds of the present invention represent a genuine enrichment of the art.

On the basis of their strong initial insecticidal activity, insecticidal compounds, according to the invention, may be used in low dosages in controlling pests. The amount of dosage depends on a variety of factors, for example, the substance used, the kind of pest, the formulation used, the state of the crop infected with the pest and the prevailing weather conditions. In general, for the control of pests in agriculture and horticulture, a dosage corresponding to from about 10 g to about 1000 g of the active substance per hectare may be used and from about 50 g to about 250 g per hectare of the active substance is preferred.

The compounds of the present invention, for practical applications, can be utilized in the form of compositions or formulations. In these compositions and formulations, the active substance is mixed with conventional inert (i.e., plant compatible and/or pesticidally inert) diluents or extenders such as solid carrier material or liquid carrier material of the type usable in conventional compositions or formulations. If desired, adjuvants such as surfactants, stabilizers, antifoam agents and antidrift agents may also be combined. Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as a diluent, organic solvents may be added as auxiliary solvents.

The active compounds of the present invention may be employed alone or in the form of mixtures with one another and/or with such solid and/or liquid dispersible carrier vehicles and/or with other known compatible active agents, especially plant protection agents, such as other arthropodicides, nematocides, fungicides, bactericides, rodenticides, herbicides, fertilizers, growth-regulating agents, synergists, etc., if desired, or in the form of particular dosage preparations for specific applications made therefrom, such as solutions, emulsions, suspensions, powders, pastes and granules which are thus ready for use.

In the compositions of the present invention the active compound is generally present in an amount substantially between about 0.0001 percent and 95 percent by weight. Mixtures suitable for direct application or field application generally contemplate those in which the active compound is present in an amount substantially between about 0.0001 percent and 5 percent, preferably between about 0.001 percent and 3 percent, by weight of the mixture.

The present invention contemplates overall compositions which comprise mixtures of a conventional dispersible carrier such as (1) a dispersible inert, finely divided carrier solid, and/or (2) a dispersible carrier liquid such as an inert organic solvent and/or water, preferably including a surface-active effective amount of a carrier vehicle assistant, (e.g., a surface-active agent, such as an emulsifying agent and/or a dispersing agent), and an amount of the active compound which is effective for the purpose in question.

The active compounds can be applied as sprays by methods commonly employed, such as conventional high-gallonage hydraulic sprays, low gallonage sprays, ultra-low-volume sprays, airblast sprays, aerial sprays and dusts as is known in the art.

Furthermore, the present invention contemplates methods of selectively killing, combating or controlling pests, which comprise applying to at least one of (a) such pests and (b) the corresponding habitat thereof (i.e., the locus to be protected, for example, to a growing crop or to an area where a crop is to be grown) a correspondingly combative or toxic amount (i.e., a pesticidally effective amount) of the particular active compound of the invention alone or together with a carrier vehicle as noted above.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases, it is possible to go above or below the aforementioned concentration ranges.

In addition to the aforementioned ingredients, the preparations, according to the invention, may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol cellulose derivatives or other colloidal materials, such as casein, to improve the adherence of the pesticide to the surface to be protected.

The compounds of the invention are also useful to control insects in seeds, generally by applying an effective amount of the compound to the surface area of the seeds to be treated. This may be accomplished by varying means common in the art, such as slurrying, soaking, dusting, spraying and the like.

Compositions and formulations according to the present invention may also include known pesticidal compounds. This expands the spectrum of activity of the preparations and may give rise to synergism. The following known insecticidal, fungicidal and acaricidal compounds are suitable for use in such a combined preparation.

Insecticides such as:
1. Chlorinated hydrocarbons, for example, 2,2-bis-(p-chlorophenyl)-1,1,1-trichloroethane and hexachloroepoxyoctahydrodimethanonaphthalene;
2. Carbamates, for example, N-methyl-1-naphthyl carbamate;
3. Dinitrophenols, for example, 2-methyl-4,6-dinitrophenyl and 2-(2-butyl)-4,6-dinitrophenyl-3,3-dimethylacrylate;
4. Organic phosphorus compounds, such as dimethyl-2-methoxy-carbonyl-1-methylvinyl phosphate, O,O-diethyl-O-p-nitrophenylphosphorothioate; N-monomethylamide of O,O-dimethyldithiophosphoryl acetic acid;
5. Diphenylsulfides, for example, p-chlorobenzyl or p-chlorophenyl sulfide and 2,4,4'-5-tetrachlorodiphenylsulfide;
6. Diphenylsulfonates, for example, p-chlorophenyl benzenesulfonate;
7. Methylcarbinols, for example, 4,4-dichloro-1trichloromethylbenzhydrol;
8. Quinoxaline compounds, such as methylquinoxaline dithiocarbonate;
9. Amidines such as N'-(4-chloro-0-tolyl)-N,N-dimethylformamidine;
10. Pyrethroids such as Allethrin;
11. Biologicals such as *Bacillus thuringiensis* preparations;
12. Organic tin compounds such as tricyclohexyltin hydroxide;
Fungicides such as:
13. Organic mercury compounds, for example, phenyl mercuryacetate and methylmercurycyanoguanide;
14. Organic tin compounds, for example, triphenyltin hydroxide and triphenyltin acetate;
15. Alkylenebisdithiocarbamates, for example, zinc ethylenebisthiocarbamate and manganoethylenebisthiocarbamate; and furthermore
16. 2,4-Dinitro-6-(2-octyl-phenylcrotonate), 1-bis(dimethylamino)phosphoryl-3-phenyl-5-amino-1,2-4-triazole, 6-methylquinoxaline-2,3-dithiocarbonate, 1,4-dithioantraquinone-2,3-dicarbonitrile, N-trichloromethylthiophthalimide, N-trichloromethylthiotetrahydrophthalimide, N-(1,1,2,2-tetrachloroethyl-thio)tetrahydrophthalimide, N-dichlorofluoromethylthio-N-phenyl-N'-dimethylsulfonyldiamide and tetrachloroisophthalonitrile.

Compounds according to the present invention were evaluated for their biological activity. In evaluating the foliar insecticidal activity of the compounds of this invention, the following test procedures were employed.

A test solution containing 600 parts per million (ppm) was made by dissolving the test compound in a solvent (acetone:methanol, 1:1), adding a surfactant and then water to give an acetone:methanol:water system of 5:5:90. A 1:1 mixture of an alkylarylpolyetheralcohol (Triton ® X-155 surfactant from Rohm and Haas Company, Philadelphia, Pa.) and a modified phthalic glycerol alkyl resin (Triton ® B-1956 surfactant from Rohm and Haas Company, Philadelphia, Pa.) was utilized at the equivalent of 1 ounce per 100 gal. of test solution as a surfactant.

Analogous solutions were made by serially diluting the 600 ppm test solution with water and surfactant to give concentrations of 150, 38, 10, 2.5, 0.6, 0.15 and 0.038 ppm. Not all compounds were tested at each of the several concentrations stated above. Test concentrations of a compound were selected as those most likely to differentiate dose response of a particular compound toward a particular test insect.

Initial evaluations were made on one or more of the following pests:

| Code Symbol | Common Name | Latin Name |
| --- | --- | --- |
| SAW | Southern Armyworm | *Spodoptera eridania* |
| MBB | Mexican Bean Beetle | *Epilachna varivestis* |
| GPA | Green Peach Aphid | *Myzus persicae* |
| TSM | Two-Spotted Spider Mite | *Tetranychus urticae* |
| BW | Boll Weevil | *Anthonomus grandis* |

For the Mexican Bean Beetle and Southern Armyworm test, lima bean (*Phaseolus limensis* var. Woods' Prolific) seedlings in 3" pots were sprayed to run-off with the test solutions using a DeVilbiss atomizer at 20 psig. When dry, each plant was placed in a plastic box (7.5" long × 5.25" wide × 3.75" deep). Each box was then infested with 10 third instar larvae of either the Mexican Been Beetle or the Southern Armyworm. The box was then sealed with a lid equipped with screened ventilation holes.

All treatments were maintained under continuous fluorescent light at 80° F. on open shelves for the course of the exposure period. Plants were watered as needed and replaced with untreated plants if they were totally consumed as was the case with ineffective treatments or untreated checks or controls. Forty-eight hours aftertreatment, the percent mortality was determined for each test species and spray concentration.

For the mite test, infested bean (*Phaseolus limeanus*) leaf discs (1.25" in diameter) containing about 50 mites were placed in a Petri dish lid on a moistened piece of cotton. The leaves were then sprayed to thorough wetness with the test solution using a rotating turntable, held for twenty-four hours and then the percentage killed was determined.

For the aphid test, infested broccoli (*Brassica oleracea italica*) leaves containing about 50 aphids were placed in a Petri dish lid on a moistened piece of cotton. The leaves were then sprayed to thorough wetness with the test solution using a rotating turntable, held for twenty-four hours and then the percentage killed was determined.

For the boll weevil test, 10 adult weevils were placed in a 0.5 pint glass Mason jar containing a small cube of apple. The weevils were confined to the jar by fiberglass screen mesh secured by a screw-type rim cap. The jars were then sprayed with the test solution using a rotating turntable; directing the spray through the mesh into the jar. The percentage killed was determined after forty-eight hours.

The mortalities obtained in this manner were plotted on logarithmic probability paper. The estimated concentration eliciting a 50 percent mortality ($LC_{50}$) was established from the best eye-fitted line to the plotted mortality data.

The results of the foliar insecticidal evaluations are given in Table II. Note the selectivity of the compounds of this invention towards aphids.

TABLE II

| | Foliar Insecticidal Evaluations[1] Estimated $LC_{50}$ Values | | | | |
|---|---|---|---|---|---|
| No. | SAW | MBB | GPA | TSM | BW |
| 1. | 460 | 75 | 1.1 | >600 | 300 |
| 2. | 300 | 138 | 4.7 | >600 | 162 |
| 3. | 24 | <38 | 1.5 | 170 | 62 |
| 4. | 150 | 24 | 3.1 | 81 | 150 |
| 5. | >600 | 115 | 5.4 | 560 | >600 |
| 6. | >600 | 52 | 2.6 | 340 | >600 |
| 7. | 360 | — | 21.0 | >600 | 150 |
| 8. | 600 | 38 | 1.4 | 50 | 31 |
| 9. | >600 | 52 | 2.0 | 108 | >600 |
| 10. | >600 | 23 | 4.3 | >600 | 500 |
| 11. | >600 | >600 | 5.0 | >600 | 150 |
| 12. | 78 | 4.2 | <2.5 | 313 | 500 |
| 13. | 78 | 5 | 0.95 | 400 | 70 |
| 14. | >600 | 52 | 3.3 | 355 | >600 |
| 15. | 150 | 150 | 9.2 | >600 | 150 |

[1] Concentration in parts per million (ppm) which kills 50% of the stated insect ($LC_{50}$).

In evaluating the pesticidal activity of the compounds of the invention against hoppers, initial evaluations were made on the following pests.

| Common Name | Latin Name |
|---|---|
| Potato Leafhopper | *Empoasca fabae* |
| Apple Leafhopper | *Empoasca maligna* |
| Green Rice Leafhopper | *Nephotettix cincticeps* |
| Brown Rice Planthopper | *Nilaparvata lugens* |

For the Potato Leafhopper test, uniform-sized fava bush bean (*Vicia faba*) leaves which fit into 5-cm Petri plates were dipped in a 600 ppm test solution, air-dried and placed in 5-cm diameter tight-fitting Petri dishes lined with a moist Gelmah filter pad (1 ml water per pad). Potato Leafhopper nymphs (5 nymphs per dish) were carefully brushed into the dish and the dishes were covered. The percent mortality was determined visually three days after treatment.

For the Apple Leafhopper, the test was carried out following the same procedure using apple (*Malus sylvestris* "McIntosh") leaves in the place of fava bean leaves.

For the Green Rice Leafhopper and Brown Rice Planthopper, rice seedlings were dipped in a 600 ppm test solution, air-dried and placed in glass tubes. Adult test insects (five insects per tube) were put into the glass tubes containing the treated seedlings and the tubes were closed with cotton plugs. The percent mortality was determined visually 48 hours after treatment.

The results obtained are listed in Table III.

TABLE III

| 0-Day Residual Efficacy of Compound 1 Against Hoppers | |
|---|---|
| Pest | Percent Kill at 600 ppm |
| Potato Leafhopper | 100 |
| Apple Leafhopper | 100 |
| Green Rice Leafhopper | 100 |
| Brown Rice Planthopper | 100 |

It is to be understood that the present specification and examples are set forth by way of illustration and not limitation and that various modifications and changes may be made without departing from the spirit and scope of the present invention as defined by the appended claims.

We claim:

1. A compound of the formula

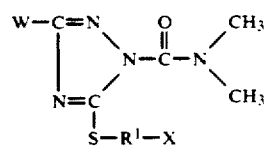

wherein

W is t-butyl, s-butyl, i-propyl, cyclopropyl, 1-methylthio-1-methylethyl or 1-methylcycloprop-1-yl;

$R^1$ is unsubstituted or substituted —$(CH_2)_n$— having from one to four of the same or different substituents independently selected from cyano, nitro, halo, —OR, —$CO_2R$, —OCOR, —COR, ($C_{2-6}$)alkenyl, ($C_2$-$C_6$)alkynyl, ($C_1$-$C_6$)alkyl, ($C_1$-$C_6$)haloalkyl and unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —$CO_2R$, —COR, —OCOR, ($C_1$-$C_4$)alkyl, ($C_1$-$C_4$)-alkoxy, ($C_1$-$C_4$)haloalkyl and ($C_2$-$C_6$)alkenyl; and X is a substituted or unsubstituted heterocycle selected from the group consisting of pyridyl, acridinyl, quinolyl, isoquinolyl and piperidinyl; where the substituent on the heterocycle is independently selected from halo, cyano, nitro, amino, —NRCOR$^2$, —COOR, —CONRR$^2$, —COR, ($C_1$-$C_4$)-alkyl, ($C_1$-$C_4$)alkoxy, ($C_1$-$C_4$)alkylthio, ($C_1$-$C_4$)haloalkyl, ($C_1$-$C_4$)haloalkoxy, ($C_1$-$C_4$)-polyhaloalkyl and ($C_1$-$C_4$)polyhaloalkoxy;

where R and $R^2$ are the same or different and are hydrogen; unsubstituted or substituted ($C_1$-$C_6$)alkyl having one to three substituents; or unsubstituted or substituted phenyl having one to three substituents; where the substituent is independently selected from halo, cyano, nitro, hydroxy, trifluoromethoxy, difluoromethoxy, tetrafluoroethoxy, trifluoromethylthio, tetrafluoroethylthio, $(C_1-C_4)$alkyl, $(C_1-C_4)$alkoxy, $(C_1-C_4)$haloalkyl, $(C_2-C_6)$alkenyl, carboxy, $(C_1-C_4)$alkoxycarbonyl;

n is an integer from one to six; and agronomically acceptable salts thereof.

2. The compound of claim 1 wherein

W is t-butyl;

$R^1$ is unsubstituted or substituted $—(CH_2)_n—$ wherein the substituent is independently selected from one to four of the same or different halo, nitro, cyano, $(C_1-C_6)$alkyl and $(C_1-C_6)$haloalkyl;

X is unsubstituted or substituted heterocycle having from one to three substituents where the substituent is independently selected from $(C_1-C_4)$alkyl and $(C_1-C_4)$haloalkyl;

n is an integer from one to six; and agronomically acceptable salts thereof.

3. The compound of claim 2 wherein $R^1$ is $—CH_2—$ or $—CH(CH_3)—$.

4. An insecticidal composition which comprises an agronomically acceptable carrier and an insecticidally effective amount of a compound of the formula $$\begin{array}{c} W-C=N \\ | \quad\quad\quad \diagdown \\ \quad\quad\quad\quad N-C-N \\ | \quad\quad\quad \diagup \quad\quad \| \quad \diagdown \\ N=C \quad\quad\quad O \quad\quad CH_3 \\ | \\ S-R^1-X \end{array} \quad\quad \begin{array}{c} CH_3 \\ \\ CH_3 \end{array}$$

wherein

W is t-butyl, s-butyl, i-propyl, cyclopropyl, 1-methylthio-1-methylethyl or 1-methylcycloprop-1-yl;

$R^1$ is unsubstituted or substituted $—(CH_2)_n—$ having from one to four of the same or different substituents independently selected from cyano, nitro, halo, $—OR$, $—CO_2R$, $—OCOR$, $—COR$, $(C_{2-6})$alkenyl, $(C_2-C_6)$alkynyl, $(C_1-C_6)$alkyl, $(C_1-C_6)$haloalkyl and unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, $—CO_2R$, $—COR$, $—OCOR$, $(C_1-C_4)$alkyl, $(C_1-C_4)$-alkoxy, $(C_1-C_4)$haloalkyl and $(C_2-C_6)$alkenyl; and X is a substituted or unsubstituted heterocycle selected from the group consisting of pyridyl, acridinyl, quinolyl, isoquinolyl and piperidinyl; where the substituent on the heterocycle is independently selected from halo, cyano, nitro, amino, is $—NRCOR^2$, $—COOR$, $—CONRR^2$, $—COR$, $(C_1-C_4)$alkyl, $(C_1-C_4)$alkoxy, $(C_1-C_4)$alkylthio, $(C_1-C_4)$haloalkyl, $(C_1-C_4)$haloalkoxy, $(C_1-C_4)$polyhaloalkyl and $(C_1-C_4)$polyhaloalkoxy;

where R and $R^2$ are the same or different and are hydrogen; unsubstituted or substituted $(C_1-C_6)$alkyl having one to three substituents; or unsubstituted or substituted phenyl having one to three substituents; where the substituent is independently selected from halo, cyano, nitro, hydroxy, trifluoromethoxy, difluoromethoxy, tetrafluoroethoxy, trifluoromethylthio, tetrafluoroethylthio, $(C_1-C_4)$alkyl, $(C_1-C_4)$alkoxy, $(C_1-C_4)$haloalkyl, $(C_2-C_6)$alkenyl, carboxy, $(C_1-C_4)$alkoxycarbonyl;

n is an integer from one to six; and agronomically acceptable salts thereof.

5. The composition of claim 4 wherein

W is t-butyl;

$R^1$ is unsubstituted or substituted $—(CH_2)_n—$ wherein the substituent is independently selected from one to four of the same or different halo, nitro, cyano, $(C_1-C_6)$alkyl and $(C_1-C_6)$haloalkyl;

X is unsubstituted or substituted heterocycle having from one to three substituents where the substituent is independently selected from $(C_1-C_4)$alkyl and $(C_1-C_4)$haloalkyl;

n is an integer from one to six; and agronomically acceptable salts thereof.

6. The compound of claim 5 wherein $R^1$ is $—CH_2—$ or $—CH(CH_3)—$.

7. The composition of claim 4 wherein the compound is present at from about 0.0001 to about 99 percent by weight of the composition.

8. The composition of claim 7 wherein the compound is present at from about 0.001 to about 90 percent by weight of the composition.

9. The composition of claim 8 wherein the compound is present at from about 0.01 to about 75 percent by weight of the composition.

10. A method of controlling insects which comprises contacting the insects with an insecticidally effective amount of a compound of the formula $$\begin{array}{c} W-C=N \\ | \quad\quad\quad \diagdown \\ \quad\quad\quad\quad N-C-N \\ | \quad\quad\quad \diagup \quad\quad \| \quad \diagdown \\ N=C \quad\quad\quad O \quad\quad CH_3 \\ | \\ S-R^1-X \end{array} \quad\quad \begin{array}{c} CH_3 \\ \\ CH_3 \end{array}$$

wherein

W is t-butyl, s-butyl, i-propyl, cyclopropyl, 1-methylthio-1-methylethyl or 1-methylcycloprop-1-yl;

$R^1$ is unsubstituted or substituted $—(CH_2)_n—$ having from one to four of the same or different substituents independently selected from cyano, nitro, halo, $—OR$, $—CO_2R$, $—OCOR$, $—COR$, $(C_{2-6})$alkenyl, $(C_2-C_6)$alkynyl, $(C_1-C_6)$alkyl, $(C_1-C_6)$haloalkyl and unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, $—CO_2R$, $—COR$, $—OCOR$, $(C_1-C_4)$alkyl, $(C_1-C_4)$-alkoxy, $(C_1-C_4)$haloalkyl and $(C_2-C_6)$alkenyl; and X is a substituted or unsubstituted heterocycle selected from the group consisting of pyridyl, acridinyl, quinolyl, isoquinolyl and piperidinyl; where the substituent on the heterocycle is independently selected from halo, cyano, nitro, amino, is $—NRCOR^2$, $—COOR$, $—CONRR^2$, $—COR$, $(C_1-C_4)$alkyl, $(C_1-C_4)$alkoxy, $(C_1-C_4)$alkylthio, $(C_1-C_4)$haloalkyl, $(C_1-C_4)$haloalkoxy, $(C_1-C_4)$polyhaloalkyl and $(C_1-C_4)$polyhaloalkoxy;

where R and $R^2$ are the same or different and are hydrogen; unsubstituted or substituted $(C_1-C_6)$alkyl having one to three substituents; or unsubstituted or substituted phenyl having one to three substituents; where the substituent is independently selected from halo, cyano, nitro, hydroxy, trifluoromethoxy, difluoromethoxy, tetrafluoroethoxy, trifluoromethylthio, tetrafluoroethylthio, $(C_1-C_4)$alkyl, $(C_1-C_4)$alkoxy, $(C_1-C_4)$haloalkyl, $(C_2-C_6)$alkenyl, carboxy, $(C_1-C_4)$alkoxycarbonyl;

n is an integer from one to six; and
agronomically acceptable salts thereof.

11. The compound of claim 10 wherein
W is t-butyl;
$R^1$ is unsubstituted or substituted —$(CH_2)_n$— wherein the substituent is independently selected from one to four of the same or different halo, nitro, cyano, $(C_1-C_6)$alkyl and $(C_1-C_6)$haloalkyl;
X is unsubstituted or substituted heterocycle having from one to three substituents where the substituent is independently selected from $(C_1-C_4)$alkyl and $(C_1-C_4)$haloalkyl;
n is an integer from one to six; and
agronomically acceptable salts thereof.

12. The compound of claim 11 wherein
$R^1$ is —$CH_2$— or —$CH(CH_3)$—.

13. The method of claim 10 wherein the insects are of the order Homoptera.

14. The method of claim 13 wherein the insects are aphids (Sternorrhyncha).

15. The method of claim 13 wherein the insects are hoppers (Auchenorrhyncha).

16. The method of claim 13 wherein the compound is applied at from about 10 g to about 5000 g per hectare.

17. The method of claim 13 wherein the compound is applied at from about 50 g to about 2500 g per hectare.

18. The compound of claim 1 which is selected from the group consisting of:
1-dimethylcarbamoyl-3-t-butyl-5-(pyrid-3-yl-methylthio)-1H-1,2,4triazole,
1-dimethylcarbamoyl-3-t-butyl-5-(pyrid-2-yl-methylthio)-1H-1,2,4triazole,
1-dimethylcarbamoyl-3-t-butyl-5-(pyrid-4-yl-methylthio)-1H-1,2,4triazole, and
1-dimethylcarbamoyl-3-t-butyl-5-(quinol-2-yl-methylthio)-1H-1,2,4triazole.

19. The compound of claim 4 which is selected from the group consisting of:
1-dimethylcarbamoyl-3-t-butyl-5-(pyrid-3-yl-methylthio)-1H-1,2,4triazole,
1-dimethylcarbamoyl-3-t-butyl-5-(pyrid-2-yl-methylthio)-1H-1,2,4triazole,
1-dimethylcarbamoyl-3-t-butyl-5-(pyrid-4-yl-methylthio)-1H-1,2,4triazole, and
1-dimethylcarbamoyl-3-t-butyl-5-(quinol-2-yl-methylthio)-1H-1,2,4triazole.

20. The compound of claim 10 which is selected from the group consisting of:
1-dimethylcarbamoyl-3-t-butyl-5-(pyrid-3-yl-methylthio)-1H-1,2,4triazole,
1-dimethylcarbamoyl-3-t-butyl-5-(pyrid-2-yl-methylthio)-1H-1,2,4triazole,
1-dimethylcarbamoyl-3-t-butyl-5-(pyrid-4-yl-methylthio)-1H-1,2,4triazole, and
1-dimethylcarbamoyl-3-t-butyl-5-(quinol-2-yl-methylthio)-1H-1,2,4triazole.

* * * * *

UNITED STATES PATENT AND TRADEMARK OFFICE
CERTIFICATE OF CORRECTION

PATENT NO. : 5,120,745
DATED : June 9, 1992
INVENTOR(S) : R. Jacobson, et al.

It is certified that error appears in the above-identified patent and that said Letters Patent is hereby corrected as shown below:

Title page, item (73) Assignee: should read --Shell Research Limited--

Signed and Sealed this

Fifth Day of September, 2000

Attest:

Q. TODD DICKINSON

*Attesting Officer*  *Director of Patents and Trademarks*